US 6,815,554 B2

(12) United States Patent
Pfeiffer et al.

(10) Patent No.: US 6,815,554 B2
(45) Date of Patent: Nov. 9, 2004

(54) PROCESS FOR PREPARING UNSATURATED ORGANOSILICON COMPOUNDS

(75) Inventors: Juergen Pfeiffer, Burghausen (DE); Peter John, Burghausen (DE)

(73) Assignee: Wacker-Chemie GmbH, Munich (DE)

( * ) Notice: Subject to any disclaimer, the term of this patent is extended or adjusted under 35 U.S.C. 154(b) by 521 days.

(21) Appl. No.: 10/119,996

(22) Filed: Apr. 10, 2002

(65) Prior Publication Data
US 2002/0151736 A1 Oct. 17, 2002

(30) Foreign Application Priority Data
Apr. 12, 2001 (DE) .......................... 101 18 489

(51) Int. Cl.$^7$ ................................................. C07F 7/08
(52) U.S. Cl. ................................... 556/440; 556/437
(58) Field of Search ................................ 556/437, 440

(56) References Cited

U.S. PATENT DOCUMENTS

| 5,117,027 A | | 5/1992 | Bernhardt et al. |
| 5,789,611 A | * | 8/1998 | Isoyama et al. ............. 556/440 |
| 6,111,126 A | * | 8/2000 | Tachikawa et al. ...... 556/440 X |

FOREIGN PATENT DOCUMENTS

| DE | 2851456 | 9/1982 |
| DE | 3832621 | 9/1989 |
| EP | 0242627 | 3/1987 |
| EP | 0 242 627 A2 | 10/1987 |
| EP | 0 437 653 A1 | 7/1991 |
| EP | 0 483 480 A1 | 5/1992 |
| EP | 0437653 | 9/1994 |
| EP | 1 004 587 A2 | 5/2000 |

OTHER PUBLICATIONS

Patent Abstract of Japan, vol. 005, No. 180 (C–079), Nov. 19, 1981 Corresponding To JP 56104890A.
Patent Abstracts of Japan, vol. 011, No. 246 (C–439) Aug. 11, 1987 Corresponding To JP 62053995A.
Patent Abstracts of Japan, vol. 011, No. 379 (C–463), Dec. 10, 1987 Corresponding To JP 62149687A.
Database WP1, Section Ch., Week 197731, Derwent Publications Ltd., London, GB, AN 1977–54813Y.
English Derwent Abstract AN 2000–378154 [33] Corresponding To EP 1 004 587.

* cited by examiner

*Primary Examiner*—Paul F. Shaver
(74) *Attorney, Agent, or Firm*—Brooks & Kushman P.C.

(57) ABSTRACT

A process for preparing unsaturated organosilanes containing organic carbonyloxy groups and having the formula $$(R^1O)_{3-n}R^2{}_nSi\text{—}X\text{—}OC(O)C(R^3)\text{=}CR^3{}_2 \qquad (I),$$

where $R^1$, $R^2$, and $R^3$ are hydrocarbon groups optionally containing interspersed ether linkages, and optionally substituted, X is an alkylene group, optionally containing ether linkages, and n is 0 to 3, by reacting haloorganofunctional silicon compounds of the formula $$(R^1O)_{3-n}R^2{}_nSi\text{—}X\text{—}Y \qquad (II),$$

where Y is a halogen atom, with a salt of an unsaturated organic carboxylic acid of the formula $$M^+[^-OC(O)C(R^3)\text{=}CR^3{}_2]_o \qquad (III),$$

where M is an alkali or alkaline earth metal and o is 0 or 1 depending on the valence of M, in the presence of a phosphonium salt as phase transfer catalyst.

12 Claims, No Drawings

PROCESS FOR PREPARING UNSATURATED ORGANOSILICON COMPOUNDS

BACKGROUND OF THE INVENTION

1. Field of the Invention

The invention relates to a process for preparing unsaturated organosilicon compounds containing organic carbonyloxy groups in the presence of phosphonium salts as phase transfer catalysts.

2. Background Art

Silicon compounds containing unsaturated organic carbonyloxy functions, e.g. 3-methacryloxypropyltrimethoxysilane, are widely employed as bonding agents between inorganic and organic materials, e.g. in sizes for glass fibers, or as crosslinkers in organic polymers.

Various methods of preparing such compounds are known. Thus, for example, DE 2851456 C2 describes the hydrosilylation of chlorosilanes containing SiH bonds by means of unsaturated organic molecules such as allyl methacrylate in the presence of metal catalysts to form chlorosilanes containing corresponding unsaturated organic functional groups. The disadvantage of this process is the fact that the subsequent alcoholysis step necessary to obtain the corresponding alkoxy-functionalized silanes generally cannot be carried out continuously due to the high tendency of the unsaturated organic functionality to polymerize.

Apart from the foregoing process, the direct reaction of an alkoxysilane containing SiH bonds with unsaturated organic molecules in the presence of metal catalysts is also known, e.g. from DE 38 32 621 C1. However, this process has the serious disadvantage that the alkoxysilanes necessary for carrying out the process present safety risks due to high toxicity and a tendency to decompose.

In EP 242 627 A2 and EP 437 653 B1, unsaturated organosilicon compounds are obtained by a nucleophilic substitution reaction between a metal or ammonium salt of an unsaturated organic acid and a haloorganofunctionalized silane. The unsaturated organic acid salts may be obtained in various ways. In the process described in EP 242 627 A2, the unsaturated organic acid is reacted with a tertiary amine to provide the ammonium salt which can be immediately reacted in the same reaction vessel with the haloorganosilicon compound. However, a significant disadvantage of this process is the low reactivity of the ammonium salts of unsaturated organic acids, which thus requires very long reaction times and the attendant serious risk of polymerization of the product.

Two alternative methods are described in EP 437 653 B1. In one process, the isolated sodium or potassium salt of the unsaturated organic acid is used. This has the disadvantage that this salt must be synthesized in a dedicated process and then dried in costly fashion. Alternatively, the metal salt of the unsaturated organic acid may be obtained by reaction of the corresponding metal alkoxide with the unsaturated organic acid, in the corresponding alcohol. After addition of the haloorganofunctionalized silicon compound and removal of the alcohol by distillation, further reaction can then be carried out in the same reaction vessel. This process has the disadvantage that the metal alkoxides used are generally corrosive, highly reactive, and very expensive. Moreover, large amounts of the respective and sometimes toxic alcohol are required as solvent, which significantly reduces the attractiveness of this process.

SUMMARY OF THE INVENTION

The present invention provides an economical route to unsaturated organosilicon compounds containing carbonyloxy groups by reacting a haloalkylsilane with a salt of an unsaturated carboxylic acid in the presence of a phase transfer catalyst.

DETAILED DESCRIPTION OF THE PREFERRED EMBODIMENT(S)

The invention provides a process for preparing unsaturated organosilanes containing organic carbonyloxy groups having the formula

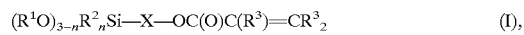

$$(R^1O)_{3-n}R^2{}_nSi-X-OC(O)C(R^3)=CR^3{}_2 \qquad (I),$$

where
R$^1$ may be identical or different and are each a monovalent, substituted or unsubstituted hydrocarbon radical which has from 1 to 10 carbon atoms optionally interrupted by oxygen atoms, R$^2$ may be identical or different and are each a monovalent, SiC-bonded, substituted or unsubstituted hydrocarbon radical which has from 1 to 10 carbon atoms optionally interrupted by oxygen atoms, or a sil(oxan)yl radical, X is a divalent, substituted or unsubstituted hydrocarbon radical which has from 1 to 40 carbon atoms optionally interrupted by oxygen atoms, R$^3$ may be identical or different and are each a hydrogen atom or a monovalent, substituted or unsubstituted hydrocarbon radical which has from 1 to 40 carbon atoms optionally interrupted by oxygen atoms, and n is 0, 1, 2 or 3;
by reacting haloorganofunctional silicon compounds of the formula

$$(R^1O)_{3-n}R^2{}_nSi-X-Y \qquad (II),$$

where R$^1$, R$^2$, X and n are as defined above and Y is a halogen atom, with a salt of an unsaturated organic carboxylic acid of the formula

$$M^+[^-OC(O)C(R^3)=CR^3{}_2]_o \qquad (III),$$

where R$^3$ is as defined above, M is an alkali metal or alkaline earth metal and o can be 1 or 2 depending on the valence of M, in the presence of a phosphonium salt as a phase transfer catalyst.

Examples of radicals R$^1$ include the radicals listed for radical R$^3$ which have from 1 to 10 carbon atoms. R$^1$ is preferably a hydrocarbon radical which has from 1 to 10 carbon atoms, optionally interrupted by oxygen atoms, and which may additionally bear nitrogen, sulfur or phosphorus substituents, most preferably a methyl, ethyl, 2-methoxyethyl, phenyl or isopropyl radical, in particular, an ethyl or methyl radical.

Examples of radical R$^2$ include the radicals listed for radical R$^3$ which have from 1 to 10 carbon atoms, and sil(oxan)yl radicals of the formula (V) R$_3$Si—(OSiR$_2$)$_p$, where R may be identical or different and are each as defined for R$^1$, p is 0 or an integer from 1 to 100, with the proviso that the radicals R may be bound to the silicon atom either directly, i.e. SiC-bonded, or via oxygen.

The radical R$^2$ is preferably a hydrocarbon radical which has from 1 to 10 carbon atoms, optionally interrupted by oxygen atoms, and which may also bear nitrogen, sulfur or phosphorus substituents, or a sil(oxan)yl radical of the formula (V), particularly preferably a phenyl, ethyl, methyl or pentamethoxydisiloxyl radical, in particular a methyl or ethyl radical.

Examples of radical X are alkylene radicals such as the methylene, ethylene, n-propylene, isopropylene, n-butylene, isobutylene, tert-butylene, n-pentylene, isopentylene, neopentylene and tert-pentylene radicals; hexylene radicals such as n-hexylene radicals; heptylene radicals such as the n-heptylene radical; octylene radicals such as the n-octylene radical, and isooctylene radicals such as the 2,2,4-trimethylpentylene radical; nonylene radicals such as the n-nonylene radical; decylene radicals such as the n-decylene radical; dodecylene radicals such as the n-dodecylene radical; octadecylene radicals such as the n-octadecylene radical; alkenylene radicals such as the vinylene and n-propenylene radicals; arylene radicals such as the phenylene, phenylmethylene, phenylethylene, 1-phenylpropylene and 2-phenylpropylene radicals, and also (poly)alkylenoxy groups of the formula (VI) —$(CH_2)_q(OZ)_m$—, where m is an integer from 1 to 100, q is an integer from 1 to 6 and Z is an ethylene, n-propylene, isopropylene, n-butylene or isobutylene radical.

X is preferably a divalent hydrocarbon radical which has from 1 to 10 carbon atoms, optionally interrupted by oxygen atoms and which may be substituted by nitrogen, sulfur or phosphorus, particularly preferably an n-propylene, isopropylene, n-butylene, isobutylene, methylene, ethylene or p-phenylene radical, in particular a methylene or n-propylene radical.

Examples of substituted or unsubstituted hydrocarbon radicals $R^3$ are alkyl radicals such as the methyl, ethyl, n-propyl, isopropyl, 1-n-butyl, 2-n-butyl, isobutyl, tert-butyl, n-pentyl, isopentyl, neopentyl, and tert-pentyl radicals; hexyl radicals such as the n-hexyl radical; heptyl radicals such as the n-heptyl radical; octyl radicals such as the n-octyl radical, and isooctyl radicals such as the 2,2,4-trimethylpentyl radical; nonyl radicals such as the n-nonyl radical; decyl radicals such as the n-decyl radical; dodecyl radicals such as the n-dodecyl radical; octadecyl radicals such as the n-octadecyl radical; cycloalkyl radicals such as the cyclopentyl, cyclohexyl, cycloheptyl and methylcyclohexyl radicals; alkenyl radicals such as the vinyl, 1-propenyl and 2-propenyl radicals; aryl radicals such as the phenyl, naphthyl, anthryl and phenanthryl radicals; alkaryl radicals such as o-, m-, and p-tolyl radicals, xylyl radicals, and ethylphenyl radicals; and aralkyl radicals such as the benzyl radical, the α- and β-phenylethyl radicals; and also dialkylaminoalkyl radicals such as the dimethylaminomethyl, 2-dimethylaminoethyl and 2-dimethylaminopropyl radicals.

The radical $R^3$ is preferably a hydrogen atom or a hydrocarbon radical which has from 1 to 10 carbon atoms, optionally interrupted by oxygen atoms and which may bear nitrogen, sulfur or phosphorus substituents. $R^3$ is most preferably a hydrogen atom or a methyl or ethyl radical, in particular a hydrogen atom or a methyl radical.

n is preferably 0 or 1.

Y is preferably an iodine, bromine or chlorine atom, most preferably a chlorine atom.

Examples of M are alkali metals, e.g. Li, Na, K and Rb, and alkaline earth metals, e.g. Mg, Ca, Sr and Ba. M is preferably sodium or potassium, in particular potassium. When M is an alkali metal, o in the formula (III) is 1, and when M is an alkaline earth metal, o is 2.

Examples of unsaturated organosilanes of the formula (I) which contain organic carbonyloxy groups and can be prepared by the process of the invention are acryloxymethyltrimethoxysilane, acryloxymethyltriethoxysilane, acryloxymethyltriphenoxysilane, acryloxymethyltris(2-methoxyethoxy)silane, acryloxymethyltriisopropoxysilane, acryloxymethyl(dimethoxy)methylsilane, acryloxymethyl(diethoxy)methylsilane, acryloxymethyl(diphenoxy)methylsilane, acryloxymethylbis(2-methoxyethoxy)methylsilane, acryloxymethyl(diisopropoxy)methylsilane, acryloxymethyl(dimethyl)methoxysilane, acryloxymethyl(dimethyl)ethoxysilane, acryloxymethyl(dimethyl)phenoxysilane, acryloxymethyl(dimethyl)(2-methoxyethoxy)silane, acryloxymethyl(dimethyl)isopropoxysilane, methacryloxymethyltrimethoxysilane, methacryloxymethyltriethoxysilane, methacryloxymethyltriphenoxysilane, methacryloxymethyltris(2-methoxyethoxy)silane, methacryloxymethyltriisopropoxysilane, methacryloxymethyl(dimethoxy)methylsilane, methacryloxymethyl(diethoxy)methylsilane, methacryloxymethyl(diphenoxy)methylsilane, methacryloxymethylbis(2-methoxyethoxy)methylsilane, methacryloxymethyl(diisopropoxy)methylsilane, methacryloxymethyl(dimethyl)methoxysilane, methacryloxymethyl(dimethyl)ethoxysilane, methacryloxymethyl(dimethyl)phenoxysilane, methacryloxymethyl(dimethyl)(2-methoxyethoxy)silane, methacryloxymethyl(dimethyl)isopropoxysilane, 3-acryloxypropyltrimethoxysilane, 3-acryloxypropyltriethoxysilane, 3-acryloxypropyltriphenoxysilane, 3-acryloxypropyltris(2-methoxyethoxy)silane, 3-acryloxypropyltriisopropoxysilane, 3-acryloxypropyl(dimethoxy)methylsilane, 3-acryloxypropyl(diethoxy)methylsilane, 3-acryloxypropyl(diphenoxy)methylsilane, 3-acryloxypropylbis(2-methoxyethoxy)methylsilane, 3-acryloxypropyl(diisopropoxy)methylsilane, 3-acryloxypropyl(dimethyl)methoxysilane, 3-acryloxypropyl(dimethyl)ethoxysilane, 3-acryloxypropyl(dimethyl)phenoxysilane, 3-acryloxypropyl(dimethyl)(2-methoxyethoxy)silane, 3-acryloxypropyl(dimethyl)isopropoxysilane, 3-methacryloxypropyltrimethoxysilane, 3-methacryloxypropyltriethoxysilane, 3-methacryloxypropyltriphenoxysilane, 3-methacryloxypropyltris(2-methoxyethoxy)silane, 3-methacryloxypropyltriisopropoxysilane, 3-methacryloxypropyl(dimethoxy)methylsilane, 3-methacryloxypropyl(diethoxy)methylsilane, 3-methacryloxypropyl(diphenoxy)methylsilane, 3-methacryloxypropylbis(2-methoxyethoxy)methylsilane, 3-methacryloxypropyl(diisopropoxy)methylsilane, methacryloxypropyl(dimethyl)methoxysilane, 3-methacryloxypropyl(dimethyl)ethoxysilane, 3-methacryloxypropyl(dimethyl)phenoxysilane, 3-methacryloxypropyl(dimethyl)(2-methoxyethoxy)silane and 3-methacryloxypropyl(dimethyl)isopropoxysilane.

Examples of haloorganofunctional silicon compounds of the formula (II) used in the process of the invention are chloromethyltrimethoxysilane, bromomethyltrimethoxysilane, chloromethyltriethoxysilane, bromomethyltriethoxysilane, chloromethyltriphenoxysilane, bromomethyltriphenoxysilane, chloromethyltris(2-methoxyethoxy)silane, bromomethyltris(2-methoxyethoxy)silane, chloromethyltriisopropoxysilane, bromomethyltriisopropoxysilane, chloromethyl(dimethoxy)methylsilane, bromomethyl(dimethoxy)methylsilane, chloromethyl(diethoxy)methylsilane, bromomethyl(diethoxy)methylsilane, chloromethyl(diphenoxy)methylsilane, bromomethyl(diphenoxy)methylsilane, chloromethylbis(2-methoxyethoxy)methylsilane, bromomethylbis(2-methoxyethoxy)methylsilane, chloromethyl(diisopropoxy)methylsilane, bromomethyl(diisopropoxy)methylsilane, chloromethyl(dimethyl)

methoxysilane, bromomethyl(dimethyl)methoxysilane, chloromethyl(dimethyl)ethoxysilane, bromomethyl(dimethyl)ethoxysilane, chloromethyl(dimethyl)phenoxysilane, bromomethyl(dimethyl)phenoxysilane, chloromethyl(dimethyl)(2-methoxyethoxy)silane, bromomethyl(dimethyl)(2-methoxyethoxy)silane, chloromethyl(dimethyl)isopropoxysilane, bromomethyl(dimethyl)isopropoxysilane, 3-chloropropyltrimethoxysilane, 3-bromopropyltrimethoxysilane, 3-chloropropyltriethoxysilane, 3-bromopropyltriethoxysilane, 3-chloropropyltriphenoxysilane, 3-bromopropyltriphenoxysilane, 3-chloropropyltris(2-methoxyethoxy)silane, 3-bromopropyltris(2-methoxyethoxy)silane, 3-chloropropyltriisopropoxysilane, 3-bromopropyltriisopropoxysilane, 3-chloropropyl(dimethoxy)methylsilane, 3-bromopropyl(dimethoxy)methylsilane, 3-chloropropyl(diethoxy)methylsilane, 3-bromopropyl(diethoxy)methylsilane, 3-chloropropyl(diphenoxy)methylsilane, 3-bromopropyl(diphenoxy)methylsilane, 3-chloropropylbis(2-methoxyethoxy)methylsilane, 3-bromopropylbis(2-methoxyethoxy)methylsilane, 3-chloropropyl(diisopropoxy)methylsilane, 3-bromopropyl(diisopropoxy)methylsilane, 3-chloropropyl(dimethyl)methoxysilane, 3-bromopropyl(dimethyl)methoxysilane, 3-chloropropyl(dimethyl)ethoxysilane, 3-bromopropyl(dimethyl)ethoxysilane, 3-chloropropyl(dimethyl)phenoxysilane 3-bromopropyl(dimethyl)phenoxysilance, 3-chloropropyl(dimethyl)(2-methoxyethoxy)silane, 3-bromopropyl(dimethyl)(2-methoxyethoxy)silane, 3-chloropropyl(dimethyl)isopropoxysilane, 3-bromopropyl(dimethyl)isopropoxysilane.

The silicon compound of the formula (II) is preferably chloromethyltrimethoxysilane, chloromethyltriethoxysilane, chloromethyl(dimethoxy)methylsilane, chloromethyl(diethoxy)methylsilane, chloromethyl(dimethyl)methoxysilane, chloromethyl(dimethyl)ethoxysilane, 3-chloropropyltrimethoxysilane, 3-chloropropyltriethoxysilane, 3-chloropropyl(dimethoxy)methylsilane, 3-chloropropyl(diethoxy)methylsilane, 3-chloropropyl(dimethyl)methoxysilane and 3-chloropropyl(dimethyl)ethoxysilane, with particular preference being given to chloromethyltrimethoxysilane, chloromethyl(dimethoxy)methylsilane, 3-chloropropyltriethoxysilane, 3-chloropropyltrimethoxysilane, and 3-chloropropyl(dimethoxy)methylsilane. The haloorganofunctional silicon compounds of the formula (II) are commercial products or can be prepared by methods customary in chemistry.

Examples of the salts of an unsaturated organic carboxylic acid of the formula (III) are potassium acrylate, potassium methacrylate, sodium acrylate, sodium methacrylate, potassium trans-but-2-enoate, potassium cis-but-2-enoate, sodium trans-but-2-enoate, sodium cis-but-2-enoate, potassium trans-2-methylbut-2-enoate, potassium cis-2-methylbut-2-enoate, sodium trans-2-methylbut-2-enoate and sodium cis-2-methylbut-2-enoate. The salts of the formula (III) are commercial products or can be prepared by methods customary in chemistry.

The salts of the formula (III) are preferably ones which are obtained by reacting an aqueous solution of a metal hydroxide (i) of the formula (VII) M(OH)$_k$, where M is as defined above and k is 1 or 2 depending on the valence of M, with an unsaturated organic carboxylic acid (ii) of the formula $$HOC(O)C(R^3)=CR^3{}_2 \qquad (IV),$$

where $R^3$ is as defined above, in the presence of an organic solvent (iii) which forms an azeotrope with water and forms a two-phase system with water in the liquid state, followed by a) removing the water by azeotropic distillation and additionally followed by b) separating off from 10 to 100% by weight of the organic solvent used by distillation.

The salt of an unsaturated carboxylic acid which has been obtained in this way, possibly in admixture with remaining organic solvent (iii), can then advantageously be used directly, without further work-up steps, in the process of the invention as compound of the formula (III). This process is highly advantageous, in that the preparation of the salt of the formula (III) used in the process of the invention, and its reaction with the silicon compounds of the formula (II), can be carried out in the same reaction vessel. Alternatively, two different reaction vessels may be used, with the salt of the unsaturated organic carboxylic acid resulting from the first reaction step, for example in the form of a suspension, being transferred without isolation, i.e. by means of a screw or a pump or any other desired method, from the first reaction vessel to the second reaction vessel in which the reaction with the compound of the formula (II) is then carried out.

The azeotropic removal of the water a) and the subsequent removal of the organic solvent by distillation b) can be carried out either at atmospheric pressure or under reduced pressure, with the pressure preferably being from 100 to 1000 hPa, more preferably from 200 to 300 hPa.

Organic solvents (iii) which can be used for the above-described preparation of the metal salt of the formula (III) used according to the invention include without limitation, aromatic hydrocarbons optionally substituted by alkyl groups, n-alkanes, isoalkanes or cycloalkanes having from 5 to 10 carbon atoms and symmetrical or unsymmetrical ethers which may contain from 2 to 10 carbon atoms and may have linear or branched alkyl groups or aryl groups, and any mixtures of these solvents.

Examples of such organic solvents (iii) are toluene, m-, o- and p-xylene and mixtures thereof, n-pentane, n-hexane, n-heptane, cyclopentane, cyclohexane, cyclooctane, cyclohexene, cis-cyclooctene, diethyl ether, tert-butyl methyl ether and di-n-butyl ether, with preference being given to n-heptane, xylenes and mixtures thereof, or toluene, most preferably toluene.

Examples of unsaturated organic acids (ii) of the formula (IV) are acrylic acid, methacrylic acid, trans-but-2-enoic acid, cis-but-2-enoic acid, trans-2-methylbut-2-enoic acid and cis-2-methylbut-2-enoic acid.

The molar ratio of the unsaturated organic acid (ii) to the metal hydroxide (i) of the formula (VII) can be from 0.5 to 2, preferably from 0.8 to 1.2 and more preferably 1, when k=1. When k=2, this molar ratio can be from 1 to 3, preferably from 1.5 to 2.5 and more preferably 2.

If the salt of the formula (III) is used in admixture with organic solvent (iii), the solvent can be entirely or partly removed from the reaction mixture according to the invention by distillation, if appropriate by rectification, either at atmospheric pressure or under reduced pressure, preferably at a pressure of from 200 to 300 hPa.

The reaction of the salt of the unsaturated organic acid of the formula (III) with a haloorganofunctional silicon compound of the formula (II) is preferably carried out at temperatures of from 60 to 150° C., more preferably from 70 to 120° C., and preferably at a pressure of from 100 to 1000 hPa, more preferably from 200 to 300 hPa.

In the process of the invention, the molar ratio of the salt of the formula (III) to the haloorganofunctional silicon compound of the formula (II) is preferably from 0.5 to 1.5, more preferably from 0.9 to 1.1, and most preferably from 1 to 1.05.

The process can be carried out in air or under an inert gas atmosphere. In the present process, an inert gas is a gas which is unreactive toward the components present in the reaction mixture under the prevailing reaction conditions, e.g. nitrogen or argon or a mixture thereof. The process is preferably carried out under an inert gas atmosphere, more preferably under a nitrogen atmosphere. If desired, the reaction can also be carried out under a nitrogen atmosphere containing from 0.1 to 2 percent of oxygen.

The process is preferably carried out in the substantial absence of water, which can be achieved by customary methods for removing traces of water from the components present in the reaction vessel, for example by drying the organic solvent or through the aid of the inert gas atmosphere, by using dry gases, etc.

In the inventive process, a phase transfer catalyst is preferably used in an amount of from 0.1 to 20 percent by weight, more preferably from 0.5 to 5 percent by weight, and most preferably from 0.8 to 2 percent by weight, in each case based on the amount of haloorganofunctional silicon compound of the formula (II).

Examples of phase transfer catalysts include quaternary phosphonium salts such as tetra-n-butylphosphonium bromide, tetra-n-butylphosphonium chloride, methyltri-n-butylphosphonium chloride, methyltri-n-butylphosphonium bromide, n-butyltriphenylphosphonium bromide, n-butyltriphenylphosphonium chloride, methyltriphenylphosphonium chloride and methyltriphenylphosphonium bromide, with particular preference being given to methyltriphenylphosphonium chloride, n-butyltriphenylphosphonium bromide and tetra-n-butylphosphonium bromide.

The reaction of the haloorganofunctional compound of the formula (II) with the salts of the formula (III) can be carried out in the presence or absence of an organic solvent, but use of an organic solvent, in particular a polar aprotic solvent, is preferred. When an organic solvent is used, the amount is preferably from 5 to 300 percent by weight, more preferably from 10 to 100 percent by weight, and most preferably from 20 to 50 percent by weight, in each case based on the amount of haloorganic silicon compound of the formula (II).

Examples of organic, polar aprotic solvents include those which aid the reaction, for instance acetone, N,N-dimethylformamide, dimethyl sulfoxide, N-methyl-2-pyrrolidone, γ-butyrolactone, diethylene glycol dimethyl ether and diethylene glycol diethyl ether, with preference being given to acetone, N,N-dimethylformamide and N-methyl-2-pyrrolidone, most preferably N,N-dimethylformamide.

If desired, the process may be carried out in the presence of inhibitors, i.e. compounds which prevent the undesirable polymerization of the target compounds via the unsaturated organic function. Preference is given to using such inhibitors. Examples of inhibitors which can be used include aromatic amines, quinones, hydroquinones, sterically hindered phenols, or stable free radicals, e.g. N,N'-diphenyl-p-phenylenediamine, N,N '-di-β-naphthyl-p-phenylenediamine, phenothiazine, hydroquinone, hydroquinone monomethyl ether, 2,6-di-tertbutylphenol, 2,6-di-tert-butyl-4-methylphenol, 2,6-di-tert-butyl-4-(N,N-dimethylamino)methylphenol and 2,2,6,6-tetramethylpiperidyl-N-oxide.

When inhibitors are used, the amounts are preferably from 0.01 to 1% by weight, more preferably from 0.05 to 0.4% by weight, in each case based on the amount of the haloorganofunctionalized silicon compound of the formula (II).

Apart from haloorganofunctional silicon compounds of the formula (II), a salt of an unsaturated organic carboxylic acid of the formula (III), a phosphonium salt as phase transfer catalyst, optionally organic solvent(s) and inhibitor (s), it is also possible to use further additives customary for nucleophilic substitution reactions. Examples of such customary additives are alkali metal iodides. Otherwise, preference is given to using no further materials.

The components used can in each case be one type of such a component or a mixture of two or more types of a respective component. The components can be mixed with one another in any order. After the reaction has reached the desired degree of completion, the resulting unsaturated organosilicon compounds containing organic carbonyloxy groups can be isolated and purified by methods known per se, i.e. by filtration or centrifugation to remove the metal halide formed, by distillation, rectification, thin film distillation, etc. The product unsaturated organosilicon compounds containing organic carbonyloxy groups can be used for all purposes for which such compounds have been used hitherto.

In a preferred embodiment, haloorganofunctional silicon compounds of the formula (II) are reacted with a salt of an unsaturated organic carboxylic acid of the formula (III) in the presence of a phosphonium salt as phase transfer catalyst, a polar aprotic organic solvent and an inhibitor.

In a particularly preferred embodiment of the process of the invention, haloorganofunctional silicon compounds of the formula (II) are reacted with a salt of an unsaturated organic carboxylic acid of the formula (III) in the presence of a phosphonium salt as phase transfer catalyst, a polar aprotic organic solvent and an inhibitor, where the salt of the formula (III) is prepared by reacting an aqueous solution of a metal hydroxide (i) of the formula (VII) with an unsaturated organic carboxylic acid (ii) of the formula (IV) in the presence of an organic solvent (iii) which forms an azeotrope with water and forms a two-phase system with water in the liquid state, followed by a) removing substantially all the water by azeotropic distillation and additionally followed by b) separating off from 10 to 100% by weight of the organic solvent used by distillation. The term "substantial" refers to removal of water such that the amount of water remaining does not adversely affect subsequent steps of the process.

The process can be carried out batchwise or continuously. The process has the advantage that it is simple to carry out and enables unsaturated organosilicon compounds containing organic carbonyloxy groups to be prepared in an efficient and inexpensive manner and in high yields and purities. The process has the particular advantage that the use of phosphonium salts as phase transfer catalysts results in formation of substantially no decomposition products during the reaction, which enables obtaining a highly pure product significantly easier. The process has the further advantage that the use of phosphonium salts as phase transfer catalysts in combination with the use of polar aprotic solvents makes it possible to obtain the target products of the formula (I) in an exceptionally short time under very mild conditions.

The use of salts of the formula (III) which have been prepared by the above-described reaction of metal hydroxides (i) and unsaturated carboxylic acids (ii) combined with azeotropic removal of the water and subsequent removal of the organic solvent (iii) has, when using compounds of the formula (II) in which $n \leq 2$, the particular advantage that it is possible to avoid undesirable hydrolysis/condensation reactions which would lead to formation of oligosiloxanes or polysiloxanes, resulting not only in a decrease in the yield of target product, but also in the formation of solid and liquid by-products which are difficult to remove. Furthermore, all solvents used in the process of the invention can be reused, which results in an environmentally friendly process with particularly sparing utilization of resources.

In the following examples, all parts and percentages are, by weight, unless indicated otherwise, and are carried out at the pressure of the surrounding atmosphere, i.e. at about 1,000 hPa, and at room temperature, i.e. about 20° C., or at a temperature which is established on combining the reactants at room temperature without additional heating or cooling. All viscosities reported in the examples are as measured at a temperature of 25° C. All reactions described in the examples were carried out under an inert gas atmosphere comprising nitrogen.

EXAMPLE 1

448.8 g (8 mol) of potassium hydroxide are dissolved in 400 g of water, covered with 2,000 g of toluene and neutralized with 688.1 g (8 mol) of methacrylic acid. After reducing the pressure to 250 hPa, all water is removed with the aid of a water separator. 1,800 g of toluene are then distilled from the reaction mixture. The suspension obtained in this way has a water content of 0.05% by weight.

After addition of a solution of 2.1 g of N,N'-diphenyl-p-phenylenediamine and 25 g of methyltriphenylphosphonium chloride in a mixture of 1,590 g (8 mol) of 3-chloropropyltrimethoxysilane and 400 g of N,N-dimethylformamide, the reaction mixture is heated at 250 hPa, and a further 400 g of toluene are distilled off until a temperature of 115° C. is reached. The mixture is then stirred for another two hours at 115° C. and 250 hPa. After filtering off the potassium chloride formed, the N,N-dimethylformamide is separated off at 50° C./5 hPa. A $^1$H-NMR spectrum of the crude product which remains indicates a product:dimer ratio of 1:0.03. The crude product is admixed with 1.7 g of 2,6-di-tert-butylphenol. Distillation at 5 hPa via a 20 cm column packed with Raschig rings at a boiling temperature of 102–103° C. gives 1,865 g of 3-methacryloxypropyltrimethoxysilane. This corresponds to a yield of 94%.

COMPARATIVE EXAMPLE 1

The procedure described in example 1 is repeated, except that the use of 25 g of methyltriphenylphosphonium chloride as a phase transfer catalyst is omitted. To complete the reaction of the 3-chloropropyltrimethoxysilane, heating for 8 hours at 115° C. is necessary. A $^1$H-NMR spectrum of the reaction solution after complete reaction indicates a product:dimer ratio of 1:0.05. 1,786 g (90%) of 3-methacryloxypropyltrimethylsilane are obtained.

COMPARATIVE EXAMPLE 2

The procedure described in example 1 is repeated, except that 25 g of tetra-n-butylammonium hydrogensulfate is used in place of 25 g of methyltriphenylphosphonium chloride. To complete the reaction of the 3-chloropropyltrimethoxysilane, heating for five hours at 115° C. is necessary. A $^1$H-NMR spectrum of the reaction solution after complete reaction indicates a product:dimer ratio of 1:0.04. 1,825 g (92%) of 3-methacryloxypropyltrimethoxysilane are obtained. The product has an unpleasant fishy odor. A $^1$H-NMR spectrum reveals the presence of 0.2% of tri-n-butylamine.

EXAMPLE 2

The procedure described in example 1 is repeated, except that toluene is not distilled off prior to addition of N,N-dimethylformamide, 3-chloropropyltrimethoxysilane, methyltriphenylphosphonium chloride and N,N'-diphenyl-p-phenylenediamine. The suspension obtained prior to the addition of N,N-dimethylformamide, 3-chloropropyltrimethoxysilane, methyltriphenylphosphonium chloride and N,N'-diphenyl-p-phenylenediamine has a water content of 0.3%.

A $^1$H-NMR spectrum of the reaction solution after complete reaction indicates a product:dimer ratio of 1:0.14. Distillation gives 1,250 g of 3-methacryloxypropyltrimethoxysilane. This corresponds to a yield of 63%.

EXAMPLE 3

The procedure described in example 1 is repeated, except that 3-chloropropyl(dimethoxy)methylsilane is used in place of 3-chloropropyltrimethoxysilane. The suspension obtained prior to the addition of N,N-dimethylformamide, 3-chloropropyl(dimethoxy)methylsilane, methyltriphenylphosphonium chloride and N,N'-diphenyl-p-phenylenediamine has a water content of 0.06%.

A $^1$H-NMR spectrum of the reaction solution after complete reaction indicates a product:dimer ratio of 1:0.04. Distillation gives 1,708 g of 3-methacryloxypropyl(dimethoxy)methylsilane. This corresponds to a yield of 92%.

EXAMPLE 4

The procedure described in example 3 is repeated, except that toluene is not distilled off before addition of N,N-dimethylformamide, 3-chloropropyl(dimethoxy)methylsilane, methyltriphenylphosphonium chloride and N,N'-diphenyl-p-phenylenediamine. The suspension obtained prior to the addition of N,N-dimethylformamide, 3-chloropropyl(dimethoxy)methylsilane, methyltriphenylphosphonium chloride and N,N'-diphenyl-p-phenylenediamine has a water content of 0.35%. A $^1$H-NMR spectrum of the reaction solution after complete reaction indicates a product:dimer ratio of 1:0.2. Distillation gives 1,040 g of 3-methacryloxypropyl(dimethoxy)methylsilane. This corresponds to a yield of 56%.

EXAMPLE 5

The procedure described in example 1 is repeated, except that chloromethyl(dimethoxy)methylsilane is used in place of 3-chloropropyltrimethoxysilane. The suspension obtained prior to the addition of N,N-dimethylformamide, chloromethyl(dimethoxy)-amethylsilane, methyltriphenylphosphonium chloride and N,N'-diphenyl-p-phenylenediamine has a water content of 0.02%.

A $^1$H-NMR spectrum of the reaction solution after complete reaction indicates a product:dimer ratio of 1:0.02. Distillation at a pressure of 5 hPa gives 1,550 g of methacryloxymethyl(dimethoxy)methylsilane at a boiling temperature of 78–80° C. This corresponds to a yield of 95%.

EXAMPLE 6

The procedure described in example 5 is repeated, except that toluene is not distilled off prior to addition of N,N-dimethylformamide, chloromethyl(dimethoxy)methylsilane, methyltriphenylphosphonium chloride and N,N'-diphenyl-p-phenylenediamine. The suspension obtained prior to the addition of N,N-dimethylformamide, chloromethyl(dimethoxy)methylsilane, methyltriphenylphosphonium chloride and N,N'-diphenyl-p-phenylenediamine has a water content of 0.38%. A $^1$H-NMR spectrum of the reaction solution after complete reaction indicates a product:dimer ratio of 1:0.24. Distillation gives 849 g of methacryloxymethyl(dimethoxy)methylsilane. This corresponds to a yield of 52%.

EXAMPLE 7

The procedure described in example 1 is repeated, except that the use of 400 g of N,N-dimethylformamide is omitted. To complete the reaction of the 3-chloropropyltrimethoxysilane, heating for ten hours at 115° C. is necessary. A $^1$H-NMR spectrum of the reaction solution after complete reaction indicates a product:dimer ratio of 1:0.06. 1,667 g (84%) of 3-methacryloxypropyltrimethoxysilane are obtained.

EXAMPLE 8

448.8 g (8 mol) of potassium hydroxide are dissolved in 400 g of water and neutralized with 688.1 g (8 mol) of methacrylic acid. The suspension obtained in this way is dried in a rotary evaporator at a temperature of 50° C. and a pressure of 20 hPa for eight hours. The potassium methacrylate obtained in this way (water content: 0.8%) is transferred into a reaction vessel blanketed with nitrogen and admixed with a solution of 2.1 g of N,N'-diphenyl-p-phenylenediamine and 25 g of methyltriphenylphosphonium chloride in a mixture of 1 590 g (8 mol) of 3-chloropropyltrimethoxysilane and 400 g of N,N-dimethylformamide. The reaction mixture is stirred at 115° C. and 250 hPa for three hours. After cooling the reaction mixture to room temperature and filtering off the potassium chloride formed, the N,N-dimethylformamide is separated off at 50° C./5 hPa. A $^1$H-NMR spectrum of the crude product which remains indicates a product:dimer ratio of 1:0.12. The crude product is admixed with 1.7 g of 2,6-di-tert-butylphenol. Distillation at 5 hPa via a 20 cm column packed with Raschig rings gives 1,349 g of 3-methacryloxypropyltrimethoxysilane at a boiling temperature of 102–103° C. This corresponds to a yield of 68%.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention. The terms "a" and "an" in the claims mean "one or more" unless indicated clearly to the contary.

What is claimed is:

1. A process for preparing unsaturated organosilanes containing organic carbonyloxy groups and having the formula $$(R^1O)_{3-n}R^2{}_n Si—X—OC(O)C(R^3)=CR^3{}_2 \quad (I),$$

where

R$^1$ may be identical or different and are each a monovalent, substituted or unsubstituted hydrocarbon radical which has from 1 to 10 carbon atoms optionally interrupted by oxygen atoms, R$^2$ may be identical or different and are each a monovalent, SiC-bonded, substituted or unsubstituted hydrocarbon radical which has from 1 to 10 carbon atoms optionally interrupted by oxygen atoms, or a sil(oxan)yl radical, X is a divalent, substituted or unsubstituted hydrocarbon radical which has from 1 to 40 carbon atoms optionally interrupted by oxygen atoms, R$^3$ may be identical or different and are each a hydrogen atom or a monovalent, substituted or unsubstituted hydrocarbon radical which has from 1 to 40 carbon atoms optionally interrupted by oxygen atoms, and n is 0, 1, 2 or 3, by reacting haloorganofunctional silicon compounds of the formula $$(R^1O)_{3-n}R^2{}_n Si—X—Y \quad (II),$$

where R$^1$, R$^2$, X and n are as defined above and Y is a halogen atom, with a salt of an unsaturated organic carboxylic acid of the formula $$M^+[^-OC(O)C(R^3)=CR^3{}_2]o \quad (III),$$

where

R$^3$ is as defined above, M is an alkali metal or alkaline earth metal and o can be 1 or 2 depending on the valence of M, in the presence of a phosphonium salt as phase transfer catalyst, and in the presence of a polar, aprotic solvent.

2. The process of claim 1, wherein the molar ratio of the salt of the formula (III) to the haloorganofunctional silicon compound of the formula (II) is from 0.5 to 1.5.

3. The process of claim 1 which is carried out under an inert gas atmosphere.

4. The process of claim 1, wherein the phase transfer catalyst is used in an amount of from 0.1 to 20 percent by weight, based on the weight of the haloorganofunctional silicon compound of the formula (II).

5. The process of claim 1, wherein the salt of the formula (III) is obtained by reacting an aqueous solution of a metal hydroxide (i) of the formula (VII) M(OH)$_k$ where k is 1 or 2 depending on the valence of M, with an unsaturated organic carboxylic acid (ii) of the formula $$HOC(O)C(R^3)=CR^3{}_2 \quad (IV),$$

in the presence of an organic solvent (iii) which forms an azeotrope with water and forms a two-phase system with water in the liquid state, further comprising a) removing water by azeotropic distillation and optionally b) removing from 10 to 100% by weight of organic solvent.

6. The process of claim 5 wherein from 10 to 100% by weight of organic solvent is removed.

7. The process of claim 1, wherein a haloorganofunctional compound (II) is reacted with a salt of an unsaturated organic carboxylic acid (III) in the presence of an organic solvent.

8. The process of claim 1, further comprising reacting said haloorganofunctional silicon compound of the formula (II) with said salt of an unsaturated organic carboxylic acid of the formula (III) in the presence of a phosphonium salt as phase transfer catalyst, a polar aprotic organic solvent and an inhibitor.

9. The process of claim 1, comprising reacting a haloorganofunctional silicon compound of the formula (II) with a salt of an unsaturated organic carboxylic acid of the formula (III) in the presence of a phosphonium salt as phase transfer catalyst, a polar aprotic organic solvent and an inhibitor, further comprising preparing the salt of the formula (III) by reacting an aqueous solution of a metal hydroxide (i) of the formula (VII) with an unsaturated organic carboxylic acid (ii) of the formula (IV) in the presence of an organic solvent (iii) which forms an azeotrope with water and forms a two-phase system with water in the liquid state, followed by a) removing the water by azeotropic distillation and subsequently b) removing from 10 to 100% by weight of the organic solvent.

10. The process of claim 1, wherein said salt of an unsaturated organic carboxylic acid (III) is prepared by reacting an unsaturated organic carboxylic acid (ii) of the formula

$$HOC(O)C(R^3)=CR^3{}_2 \qquad (IV)$$

with alkali metal hydroxide or alkaline earth metal hydroxide or a mixture thereof in water, said process further comprising employing an organic solvent which forms a two phase composition with water, and removing water by azeotropically distilling water and organic solvent from said two phase composition to form a water-depleted salt of an unsaturated organic carboxylic acid.

11. The process of claim 10, further comprising adding a polar aprotic solvent to said water-depleted salt of an unsaturated organic carboxylic acid and removing a portion of said polar aprotic solvent by distillation, thereby further reducing the water content of said water-depleted salt of an unsaturated organic carboxylic acid.

12. The process of claim 1, wherein said phase transfer catalyst comprises a tetraorganophosphonium halide.

* * * * *

UNITED STATES PATENT AND TRADEMARK OFFICE
CERTIFICATE OF CORRECTION

PATENT NO.    : 6,815,554 B2
DATED         : November 9, 2004
INVENTOR(S)   : Juergen Pfeiffer et al.

It is certified that error appears in the above-identified patent and that said Letters Patent is hereby corrected as shown below:

Column 12,
Line 59, after "in the presence of" delete "a phosphonium salt as phase transfer catalyst, a polar aprotic organic solvent and"

Signed and Sealed this

Fourth Day of January, 2005

JON W. DUDAS
*Director of the United States Patent and Trademark Office*